(12) United States Patent
Lee et al.

(10) Patent No.: US 12,220,106 B2
(45) Date of Patent: Feb. 11, 2025

(54) ENDOSCOPE HAVING FRICTION CONTROL PART

(71) Applicant: MEDINTECH INC., Seoul (KR)

(72) Inventors: Chi Won Lee, Namyangju-si (KR); Myung Joon Kim, Gwacheon-si (KR); Suk Gyu Koh, Seoul (KR)

(73) Assignee: MEDINTECH INC., Seoul (KR)

( * ) Notice: Subject to any disclaimer, the term of this patent is extended or adjusted under 35 U.S.C. 154(b) by 0 days.

(21) Appl. No.: 18/288,182

(22) PCT Filed: Dec. 5, 2022

(86) PCT No.: PCT/KR2022/019628
§ 371 (c)(1),
(2) Date: Oct. 25, 2023

(87) PCT Pub. No.: WO2023/106769
PCT Pub. Date: Jun. 15, 2023

(65) Prior Publication Data
US 2024/0225427 A1      Jul. 11, 2024

(30) Foreign Application Priority Data

Dec. 8, 2021   (KR) .................. 10-2021-0174910

(51) Int. Cl.
*A61B 1/005*      (2006.01)
*A61B 1/00*       (2006.01)

(52) U.S. Cl.
CPC ........ *A61B 1/0057* (2013.01); *A61B 1/00124* (2013.01); *A61B 1/00128* (2013.01); *A61B 1/0052* (2013.01)

(58) Field of Classification Search
CPC . A61B 1/0057; A61B 1/00124; A61B 1/0053; A61B 1/0052; A61B 1/00128
See application file for complete search history.

(56) References Cited

U.S. PATENT DOCUMENTS

2008/0262309 A1* 10/2008 Miyoshi ............... A61B 1/0052
                                                       600/146
2013/0080658 A1*  3/2013 Ferguson, Jr. ........ G06F 16/435
                                                       709/248

(Continued)

FOREIGN PATENT DOCUMENTS

JP           3029671 B2     4/2000
JP        2002325724 A  * 11/2002 ......... A61B 1/00078

(Continued)

OTHER PUBLICATIONS

International Search Report for PCT/KR2022/019628 mailed Mar. 10, 2023 from Korean Intellectual Property Office.

*Primary Examiner* — John P Leubecker
*Assistant Examiner* — Li-Ting Song
(74) *Attorney, Agent, or Firm* — Revolution IP, PLLC

(57) ABSTRACT

The present invention relates an endoscope, including: a bendable section configured to be inserted into a subject's body to collect image information; and a power transmission means configured to transmit power provided by the power source to the bendable section, wherein the power transmission means comprises a power-transmitting mechanical cord and a friction control part configured to promote or restrain a movement of the mechanical cord.

3 Claims, 9 Drawing Sheets

(56) References Cited

U.S. PATENT DOCUMENTS

| | | | |
|---|---|---|---|
| 2013/0096384 A1* | 4/2013 | Arai | G02B 23/2476 |
| | | | 600/144 |
| 2018/0235440 A1* | 8/2018 | Okamoto | A61B 1/0057 |
| 2019/0082935 A1 | 3/2019 | Kitanaka | |
| 2021/0068621 A1* | 3/2021 | Shin | A61B 1/00073 |
| 2022/0265967 A1* | 8/2022 | Alhadeff | A61B 1/0052 |
| 2023/0309802 A1* | 10/2023 | Fancher | A61B 1/0016 |
| | | | 600/104 |
| 2024/0115117 A1* | 4/2024 | Komuro | A61B 1/0052 |

FOREIGN PATENT DOCUMENTS

| | | |
|---|---|---|
| JP | 2002-360504 A | 12/2002 |
| JP | WO2017-203740 A1 | 3/2019 |
| KR | 10-2010-0137652 A | 12/2010 |
| KR | 10-2016-0010019 A | 1/2016 |

\* cited by examiner

ENDOSCOPE HAVING FRICTION CONTROL PART

TECHNICAL FIELD

The present disclosure relates to an endoscope and, more particularly, to an endoscope having a power transmission system transmitting power provided by a power source to a bendable section.

BACKGROUND ART

The information disclosed in this section is only provided for an understanding of background information of embodiments of the present disclosure and should not be taken as a description of the prior art.

An endoscope generally refers to a medical instrument for examining the interior of the body for medical purposes. Such an endoscope may be referred to as "bronchoscope," "gastric endoscope," "laparoscope," or "colonoscope" depending on the area to be examined therewith. Unlike most medical imaging devices, the endoscope is a medical device which is inserted directly into the body.

Due to the development of optical fibers and the rapid development of optical technology and electronics, endoscope technology has reached the stage of the current electronic endoscope and has made a great contribution to the development of the field of gastroenterology. With the development of the electronic endoscope, the electronic endoscope is used not only in the diagnostic field to directly look into and perform histological examinations of a subject's body, but may also replace invasive surgery due to the rapid development of various treatment endoscopes.

The configuration of the endoscope may generally include an insertion tube configured to be inserted into the patient's body with a bendable section and a flexible portion, a control body connected to one end of the insertion tube to control the bending motion of the bendable section, a connector coupled to a light source device, or the like, and a universal code spacing the control body and the connector apart from each other.

The endoscope has a structure in which a mechanical cord (or cable) is disposed between the bendable section and the control body to control the bending motion of the bendable section and the mechanical cord is connected to a control knob disposed on the control body. According to the structure of the endoscope, when the user, i.e., a doctor, manually operates the control knob, the mechanical cord transmits power to enable the bending motion of the bendable section.

While a doctor is performing an endoscope, an emergency situation fatal to the patient may occur. However, such an endoscope having the above-described structure requires a doctor to control the bending motion of the bendable section by manually operating the knob in the emergency situation, thereby causing the doctor to only focus on operating the knob. Thus, it may be difficult to overcome the emergency situation, and the bending motion of the bendable section may not be accurately performed.

Therefore, there was developed an endoscope in which the bending motion of a bendable section may be performed automatically using a power source rather than by a manual operation of a doctor. However, the endoscope with this structure may have control precision and stability problems due to the absence of an appropriate structure able to receive power from the outside of the endoscope.

In particular, in the endoscope having the above-described structure, for example, when power is required to be transmitted from the connector at one end of the endoscope to the bendable section at the other end of the endoscope, a power transmission system is longer, so power transmission may be delayed or power transmission may not be maintained uniformly, thereby causing problems with responsiveness.

The information disclosed in the Background section is technical information that the inventors possessed for, or acquired during, derivation of embodiments of the present disclosure and should not be taken as known technology disclosed to the public before the filing of the embodiments of the present disclosure.

DISCLOSURE

Technical Problem

Accordingly, the present disclosure has been made in consideration of the above-described problems occurring in the related art, and the present disclosure provides an endoscope able to restrain the movement of a power transmission system transmitting power provided by a power source to a bendable section, thereby uniformly maintaining the movement of the power transmission system and improving the response of the power transmission system.

The objectives of the present disclosure are not limited to the aforementioned descriptions, and other objectives not explicitly disclosed herein will be clearly understood by a person having ordinary knowledge in the art from the description provided hereinafter.

Technical Solution

According to an aspect of the present disclosure, an endoscope may include one or more among: a bendable section configured to be inserted into a subject's body to collect image information; and a power transmission means configured to transmit power provided by the power source to the bendable section.

The power transmission means may include a power-transmitting mechanical cord and a friction control part configured to promote the movement of the mechanical cord.

In addition, according to an aspect of the present disclosure, an endoscope may include one or more among: a bendable section configured to be inserted into a subject's body to collect image information; and a power transmission means configured to transmit power provided by the power source to the bendable section.

The power transmission means may y include a power-transmitting mechanical cord and a friction control part configured to restrain the movement of the mechanical cord.

In some embodiments, the endoscope may further include a control body connected to the bendable section and configured to control a bending motion of the bendable section and a connector connected to the control body.

One side of the power transmission means may be connected to the connector. The other side of the power transmission means may extend through the control body and be connected to the bendable section.

In some embodiments, the endoscope may further include a control body connected to the bendable section and configured to control a bending motion of the bendable section and a connector connected to the control body.

The friction control part may be provided on the control body or the connector.

In some embodiments, the power transmission means may include a guide tube surrounding the mechanical cord to guide the same. The movement-restraining friction control part may friction occurring during the movement of the control mechanical cord by adjusting the diameter of the guide tube or a tension of the guide tube.

In some embodiments, the guide tube may include a spring structure, and the movement-restraining friction control part may adjust the diameter of the spring structure by pulling or pushing the spring structure.

In some embodiments, the guide tube may include a spring structure, and the movement-restraining friction control part may adjust the tension of the guide tube by pulling or pushing the spring structure.

In some embodiments, the friction control part may include an end holding part connected to one end of the guide tube from which the mechanical cord is drawn and a fixing means on which the end holding part is disposed.

In some embodiments, the fixing means may include a position control part configured to adjust a position at which the end holding part is disposed in order to control movement restraint of the mechanical cord.

In some embodiments, the fixing means may include a fixed block and a fixing bracket fixing the end holding part to the fixed block, the fixed block may include a partition provided on one side thereof and supporting the end holding part and a plurality of fastening holes sequentially provided in the partition, and the fixing bracket may be fixedly fitted to one of the plurality of fastening holes using a fastening means.

In some embodiments, the friction control part may include a restraint control part configured to control movement restraint of the mechanical cord.

According to another aspect of the present disclosure, an endoscope may include one or more among: an insertion tube including a bendable section configured to be inserted into a subject's body and perform a bending motion;
- a control body connected to the insertion tube and configured to be held by a user; a connector connected to the control body and configured to receive power from an external source;
- a universal cord spacing the control body and the connector apart from each other; a power transmission means configured to receive power from the connector and transmit the same to the bendable section; and
- a friction providing part provided on one side of the power transmission means and configured to provide friction to the power transmission means.

According to another aspect of the present disclosure, an endoscope may include a power transmission means including a mechanical cord and a guide tube surrounding the mechanical cord to guide the same, wherein a portion of the guide tube of the power transmission means is torn to externally expose the mechanical cord, and the power transmission means includes a fixing means configured to fix separated both ends of the guide tube by pulling or pushing the same.

Advantageous Effects

According to embodiments of the present disclosure as described above, provided is the endoscope able to restrain the movement of a power transmission system transmitting power provided by a power source to a bendable section, thereby uniformly maintaining the movement of the power transmission system and improving the response of the power transmission system.

In addition, the present disclosure has a variety of effects with excellent versatility depending on the embodiment, and such effects may be clearly understood from the following description of embodiments.

DESCRIPTION OF DRAWINGS

The following drawings accompanying the specification illustrate embodiments of the present disclosure and, together with the foregoing disclosure, serve to provide further understanding of the technical spirit of the present disclosure, and thus, the present disclosure should not be construed as being limited to the drawings.

MODE FOR INVENTION

Figure 1:
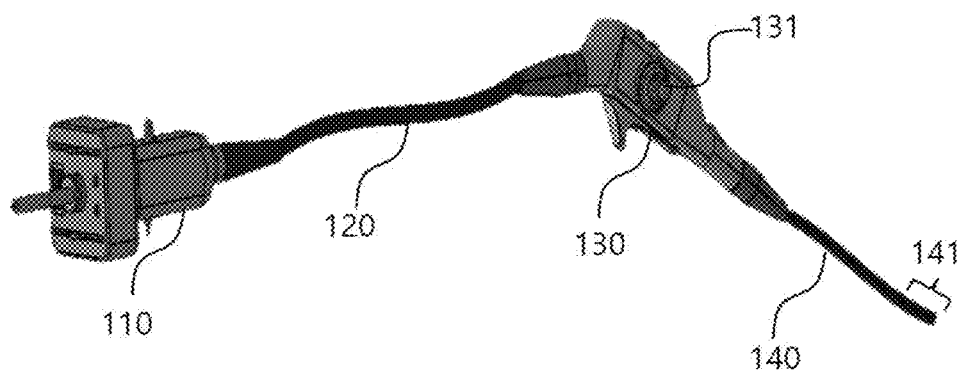
FIG. 1 illustrates the shape of an endoscope according to an embodiment of the present disclosure.

Advantages and features of the present disclosure, as well as methods of realizing the same, will be more clearly understood from the following detailed description of embodiments when taken in conjunction with the accompanying drawings. However, the present disclosure is not limited to specific embodiments to be described hereinafter but should be understood as including a variety of modifications, equivalents, and alternatives within the spirit and scope of the present disclosure. Rather, these embodiments are provided so that the description of the present disclosure will be complete and will fully convey the scope of the present disclosure to a person having ordinary skill in the art in the technical field to which the present disclosure pertains. In the following description of the present disclosure, a detailed description of related known technology will be omitted when the description may render the subject matter of the present disclosure unclear.

The terminology used in this application is used to describe specific embodiments only and is not intended to limit the invention. Expressions in the singular include the plural unless the context clearly indicates otherwise.

In the present application, the terms "includes" or "has" and the like are intended to designate the presence of the features, numbers, steps, actions, components, parts, or combinations thereof described in the specification, and are not intended to preclude the possibility of the presence or addition of one or more other features, numbers, steps, actions, components, parts, or combinations thereof. Terms such as first, second, and the like may be used to describe various components, but the components are not to be limited by such terms. Such terms are used only to distinguish one component from others Hereinafter, embodiments according to the present disclosure will be described in detail with reference to the accompanying drawings, wherein identical or corresponding components are given the same reference numerals and duplicate descriptions thereof are omitted.

Figure 2:
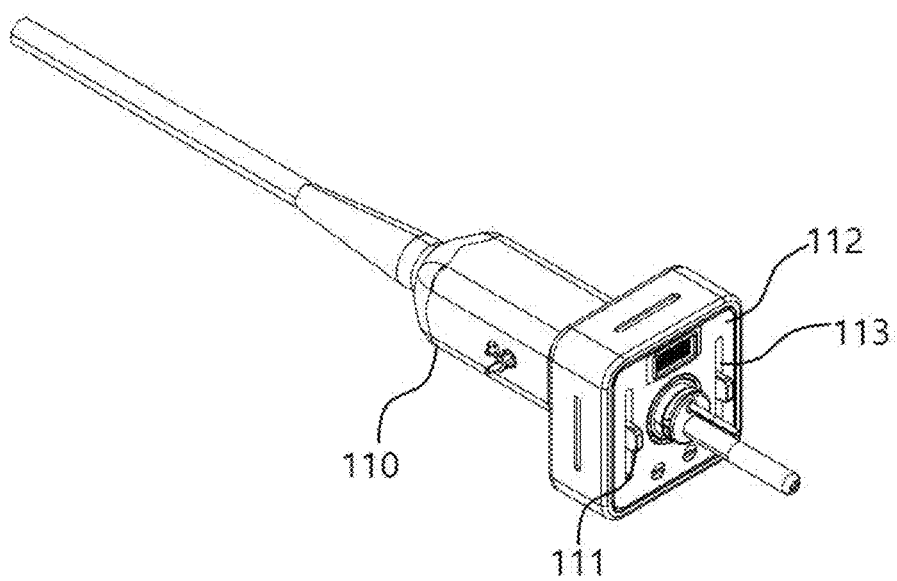
FIG. 2 illustrates the shape of the connector of the endoscope according to an embodiment of the present disclosure.

FIG. 1 illustrates the shape of an endoscope according to an embodiment of the present disclosure. FIG. 2 illustrates the shape of the connector of the endoscope according to an embodiment of the present disclosure.

Figure 3:
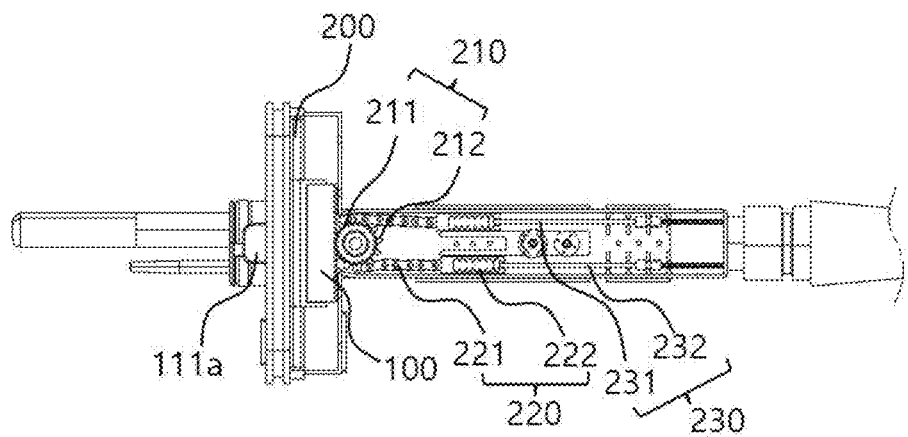
FIG. 3 illustrates the power receiving part and the power transmission part as the internal shape of the connector of FIG. 2 from which the cover is removed.
Figure 4:
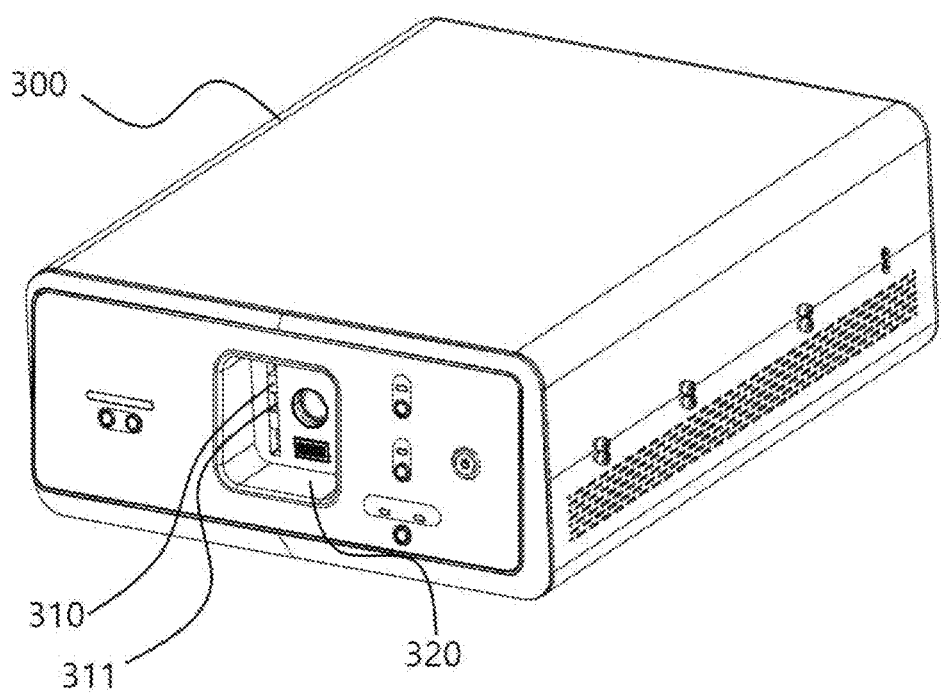
FIG. 4 illustrates the shape of a light source device to which the endoscope according to an embodiment of the present disclosure is coupled.

FIG. 3 illustrates the power receiving part and the power transmission part as the internal shape of the connector of FIG. 2 from which the cover is removed, and FIG. 4 illustrates the shape of a light source device to which the endoscope according to an embodiment of the present disclosure is coupled.

Figure 5:
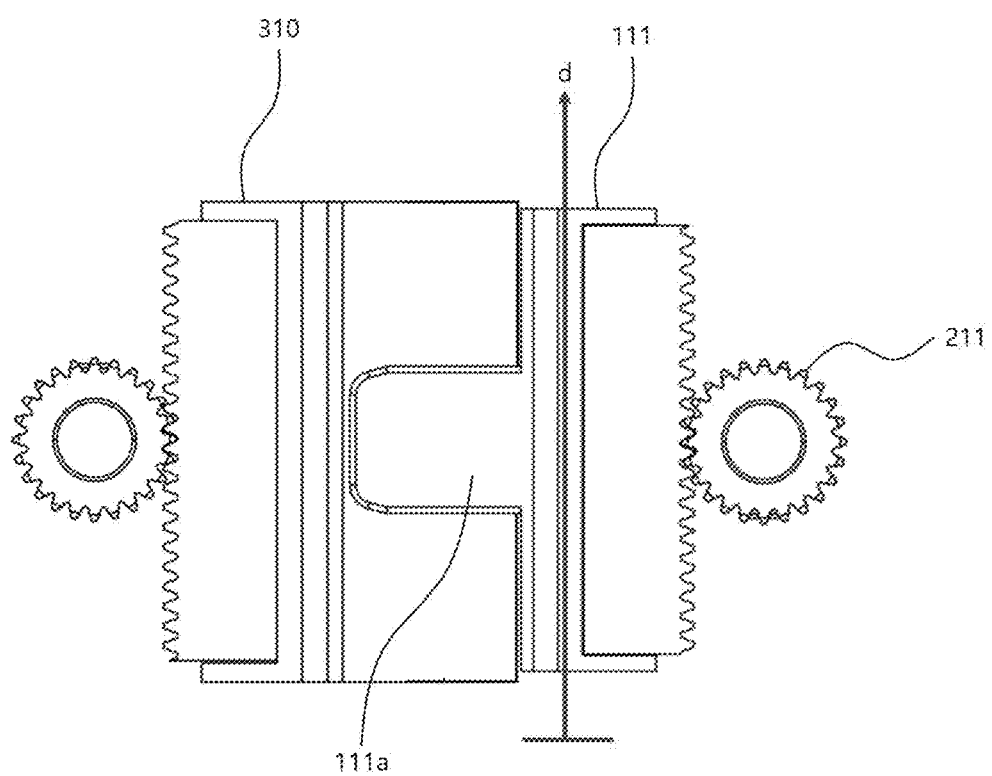
FIG. 5 illustrates a combined shape of the power providing part disposed on the light source device of FIG. 4 and the power receiving part disposed on the connector of FIG. 3.

FIG. 5 illustrates a combined shape of the power providing part disposed on the light source device of FIG. 4 and the power receiving part disposed on the connector of FIG. 3.

In some embodiments, an endoscope 100 according to an embodiment of the present disclosure may include one or more among an insertion tube 140, a control body 130, and a universal cord 120, and a connector 110.

In some embodiments, the control body 130 may be disposed between one end of the insertion tube 140 and one end of the universal cord 120, and the connector 110 may be connected to the other end of the universal cord 120.

The insertion tube 140 may be a portion that is inserted into the patient's body when a user, i.e., a doctor, performs an endoscopy on the patient using the endoscope 100. The insertion tube 140 may include a tube tip, a bendable section 141, and a flexible portion.

The tube tip may be a component configured to illuminate a target area, collect image information, perform a treatment, or the like. The tube tip may be disposed on the distal end of the insertion tube, and may include an illumination means for illuminating the interior of the subject's body, an imaging means for imaging the interior of the subject's body, a biopsy channel for collecting tissue from the interior of the subject's body, an air-water channel for spraying air, water, or the like for various purposes, and the like.

The bendable section 141 may perform a bending motion in response to the user's operation, and may be bent inside the body and travel along the interior of the curved tubular organ. The tube tip may be disposed on the distal end of the bendable section 141, and the distal end of the bendable section 141 may bend in the bending motion to place the tube tip in a direction desired by the user.

The flexible portion may be located between the bendable section 141 and the control body 130, and may be a portion that moves along with the bendable section 141 when the bendable section travels through the gastrointestinal tract inside the patient's body.

The control body 130 may be provided with a controller 131 to control the bending motion of the bendable section 141, and may be provided with a flow control valve or a flow control switch able to control a flow of air or water or suction. The controller 131 may include, for example, a joystick.

The insertion tube 140 may be connected to one side of the control body 130, and the universal cord 120 may be connected to the other side of the control body 130. The connector 110 may be connected to the distal end of the universal cord 120.

The connector 110 may serve to connect the endoscope 100 to an external device. Here, the external device may include, for example, a light source device 300, an image processing device, and the like.

When the endoscope 100 is connected to the light source device 300 or the image processing device via the connector 110, the endoscope 100 may receive light from the light source device 300 via the connector 110 and illuminate the interior of the patient's body, and the image information regarding the interior of the patient's body collected by the endoscope 100 may be transmitted to the image processing device via the connector 110.

The universal cord 120 may connect the control body 130 and the connector 110, and may serve to space the connector 110 and the control body 130 apart from each other so that a user can move easily when using the endoscope 100 by holding the control body 130. In some embodiments, the universal cord 120 may be omitted and the connector 110 may be connected to the other side of the control body 130.

According to an embodiment of the present disclosure, the endoscope 100 may include: a power receiving part 111 configured to move by receiving power from a power source; and a bendable section 141, the bending motion of which is controlled by the movement of the power receiving part 111. In some embodiments, the bendable section 141 may include an imaging means for being inserted into the subject's body to collect image information therefrom and an illumination means for illuminating the interior of the subject's body.

Here, the power source may refer to a power generating device and may include, for example, a motor. In some embodiments, the power source may be disposed in the endoscope 100. In some embodiments, the power source may be disposed outside the endoscope 100. The power source disposed outside the endoscope 100 may refer to the power source being disposed on a power providing device provided separately from the endoscope 100. In some embodiments, the power providing device may include, for example, the light source device 300 or an image processing device. In this case, the endoscope 100 may be coupled to the light source device 300 or the image processing device to move by receiving power from the light source device 300 or the image processing device.

In some embodiments, when the endoscope 100 according to the present embodiment is connected to the light source device 300 having the power source therein, the endoscope 100 may illuminate the interior of the patient's body by receiving light from the light source device 300 and perform the bending motion inside the patient's body by receiving power from the light source device 300

In addition, when the endoscope 100 is connected to the image processing device including a power source therein, the endoscope 100 may transmit collected image information collected from inside the patient's body to the image processing device. The endoscope 100 may perform the bending motion inside the patient's body by receiving power from the image processing device.

The power receiving part 111 according to the present embodiment may refer to a power receiving component. The power receiving part 111 may include a mechanical power receiving component. In some embodiments, the power receiving part 111 may receive power from an external device present outside the endoscope 100 as an article separate from the endoscope 100. In some embodiments, the power receiving part 111 may receive power directly from the light source device 300 including the power source therein.

The power receiving part 111 according to the present embodiment may be disposed on the connector 110 of the endoscope 100. When the connector 110 of the endoscope 100 is connected to the light source device 300 including the power source therein, the connector 110 may receive power from the power source of the light source device 300.

In some embodiments, a power providing part 310 supplying power to the light source device 300 may be disposed. The power providing part 310 disposed on the light source device 300 may be formed to correspond to the shape of the power receiving part 111 disposed on the connector 110. In some embodiments, the power providing part 310 may be provided with recesses 311, and the power receiving part 111 may be provided with protrusions 111a. The protrusions 111a of the power receiving part 111 may have a structure protruding outward through slots 113 formed in a front cover 112 of the connector 110.

When the connector 110 is coupled to a connector receptacle 320 of the light source device 300, the power providing part 310 and the power receiving part 111 may be coupled to each other and be ready for transmitting power from the light source device 300 to the connector 110.

There may be a variety of methods of transmitting power from the light source device 300 to the endoscope 100. In some embodiments, the power providing part 310 may have a configuration like a slider coupled to a rail structure provided on the light source device 300 to move on the rail structure. The power receiving part 111 may also have a configuration like a slider coupled to a rail structure 200 provided on the connector 110 to move on the connector 110, in the same manner as the power providing part 310.

In this structure, when the power providing part 310 moves by receiving power from the power source, the power receiving part 111 engaged with the power providing part 310 may move along with the power providing part 310, so that power may be provided by the light source device 300 to the connector 110.

The endoscope 100 according to the present embodiment may sequentially include the connector 110, the universal cord 120, the control body 130, and the insertion tube 140. Here, mechanical cords 230 may be disposed to sequentially extend through the connector 110, the universal cord 120, the control body 130, and the insertion tube 140. One side of each of the mechanical cords 230 may be connected to the power receiving part 111, and the other side of each of the mechanical cord 230 may be connected to the bendable section 141 forming one end of the insertion tube 140.

The power receiving part 111 may be connected to the mechanical cords 230 through a power transmission part. The power transmission part may include a pinion-sprocket assembly 210 and a chain-slider assembly 220.

In some embodiments, the pinion-sprocket assembly 210 may have a structure in which a pinion gear 211 and a sprocket 212 are integrally provided on a single rotating structure such that when the pinion gear 211 rotates, the sprocket 212 also rotates together. The chain-slider assembly 220 may have a structure in which a pair of sliders 222 are coupled to both ends of a chain 221, respectively, such that when the chain 221 moves, the sliders 222 connected to both ends of the chain 221, respectively, also move.

A rack gear may be provided on the rear surface of the power receiving part 111. The pinion gear 211 of the pinion-sprocket assembly 210 may be meshed with the rack gear such that power may be transmitted. In addition, in the pinion-sprocket assembly 210, the sprocket 212 may be meshed with the chain 221 of the chain-slider assembly 220 such that power may be transmitted. The mechanical cords 230 may be connected to the paired sliders 222 of the chain-slider assembly 220, respectively. In this case, a first cord 231 and a second cord 232 described below may be connected to the paired sliders 222, respectively. Due to this structure, the first cord 231 and the second cord 232 may be paired.

According to the above-described configuration of the power transmission part, when the power receiving part 111 slides, the mechanical cords 230 are pulled or pushed to transmit power to the bendable section 141, and the bendable section 141 performs the bending motion by receiving power through the mechanical cords 230. Consequently, the bending motion of the bendable section 141 may be controlled by the movement of the power receiving part 111.

In some embodiments, the control body 130 may generate a control signal. The control signal generated by the control body 130 may control the rotational force of the power source. In some embodiments, the control signal generated by the control body 130 may control the travel distance d of the power receiving part 111.

The control body 130 according to the present embodiment may be a component having dimensions and a shape by which the user may hold the control body 130 to insert the insertion tube 140 including the bendable section 141 into the interior of the subject's body or rotate the same, and may serve as a type of handle. The user may collect image information or perform a treatment inside the subject's body by adjusting the position of the bendable section 141 inside the subject's body while holding the control body 130.

In some embodiments, the control body 130 may be provided with a controller 131, for example, a control stick, generating a control signal. The control signal generated by the controller 131 may include a control command for controlling the rotational force of the power source.

When the power source is disposed on an external device, for example, the light source device 300, the control signal may be transmitted from the endoscope 100 to an external device via a wired or wireless medium.

In some embodiments, when the control signal is transmitted via a wireless medium, in an embodiment for realizing wireless transmission, a communication module may be mounted on the control body 130, and the rotational force of the power source may be controlled by transmitting the control signal to a power source controller by the communication module.

In some embodiments, when the control signal is transmitted via a wired medium, in an embodiment for realizing wired transmission, an electrical cable configuration may be connected to the control body 130, the universal cord 120, and the connector 110 in a control stick, and a control signal terminal may be disposed on one end of the connector 110.

In addition, in this case, the connector receptacle 320 of the light source device 300 may also be provided with a control signal receiving terminal, and the control signal receiving terminal may have a structure electrically connected to the power source controller.

When the connector 110 is connected to the light source device 300, the control signal terminal may be in contact with the control signal receiving terminal, and a control signal generated by the control stick may be transmitted to the power source controller through an electrical cable, the control signal terminal, and the control signal receiving terminal.

In some embodiments, a control signal generated by the controller 131 disposed on the control body 130 may control the travel distance d of the power providing part 310 of the light source device 300 or the power receiving part 111 of the connector 110.

That is, the control signal generated by the control body 130 may control the travel distance d of the power receiving part 111 by a structure in which the control signal controls the rotational force of the power source of the light source device 300, the power source generates power, and the generated power is sequentially transmitted through the power providing part 310 and the power receiving part 111.

In some embodiments, the direction of the rotation of the power source may determine the direction of the movement of the power providing part 310 or the power receiving part 111, and the speed of the rotation of the power source may determine the speed of the movement of the power providing part 310 or the power receiving part 111. In addition, the direction of the movement of the power receiving part 111 may determine the direction of the bending of the bendable section 141, and the speed of the movement of the power receiving part 111 may determine the speed of the bending of the bendable section 141.

The user, i.e., a doctor, may generate the control signal by operating the control stick and transmit the generated control signal to the power source disposed on the light source device 300. The power source that has received the control signal may generate rotational force in response to the control signal. The power providing part 310 and the power receiving part 111 may move in response to the generated rotational force. Consequently, the bending motion of the bendable section 141 may be controlled by the movement of the power receiving part 111.

In some embodiments, the power receiving part 111 may include a type of slider. The power receiving part 111 may be coupled to the rail structure 200 provided on the connector 110 to move in a specific direction on the rail structure 200. For example, the power receiving part 111 may reciprocally slide between a first end and a second end formed by the rail structure 200 provided on the connector 110.

For example, the power receiving part 111 may move within a range of bending angles (i.e., a bending angle range) of the bendable section 141 while reciprocating between the first end and the second end. Here, the first end of the power receiving part 111 may correspond to a first angle of the bending angle range, and the second end of the power receiving part 111 may correspond to a second angle of the bending angle range. For example, when the power receiving part 111 moves from the first end to the second end, the bendable section 141 may be bent from the first angle to the second angle.

The bending angle range of the bendable section 141 may be previously determined to a set value. The bending angle range of the bendable section 141 may be set such that the bending is limited, for example, between the first angle and the second angle. Accordingly, the position of the bendable section 141 may be accurately controlled by a computer through electrification of the endoscope 100, and the user, i.e., a doctor, may estimate the range of the bending of the bendable section 141.

The control signal may allow the bending motion of the bendable section 141 to precisely conform to the predetermined bending angle range by controlling the travel distance d of the power providing part 310 disposed on the light source device 300 or the power receiving part 111 disposed on the connector 110.

In some embodiments, the power receiving part 111 may include a first slider and a second slider, and the control signal may include a first control signal for controlling the travel distance d of the first slider and a second control signal for controlling the travel distance d of the second slider.

The power receiving part 111 may include a pair of components. That is, the power receiving part 111 may include a first slider and a second slider. The power providing part 310 may include a pair of components like the power receiving part 111. In the control signal, the first control signal may control the travel distance d of the first slider, and the second control signal may control the travel distance d of the second slider.

In some embodiments, the mechanical cords 230 transmitting power to the bendable section 141 may include the first cord 231, the second cord 232, a third cord, and a fourth cord.

In some embodiments, the first cord 231, the second cord 232, the third cord, and the fourth cord may be controlled by four sliders that move independently of each other.

In addition, in other embodiments, the first cord 231 and the second cord 232 may form a first set of cords, and the third cord and the fourth cord may form a second set of cords.

The first cord 231 and the second cord 232 may form the first set of cords, and the third cord and the fourth cord may form the second set of cords.

In the first set of cords, the first cord 231 and the second cord 232 have a paired structure in which when the first cord 231 is pulled, the second cord 232 is pushed and when the second cord 232 is pulled, the first cord 231 is pushed. In the second set of cords, the first cord 231 and the second cord 232 have a paired structure in which when first cord 231 is pulled, the second cord 232 is pushed and when the second cord 232 is pulled, the first cord 231 is pushed.

Here, the first set of cords may be connected to the first slider to transmit power in response to the linear movement of the first slider, and the second set of cords may be connected to the second slider to transmit power in response to the linear movement of the second slider. According to the configuration in which the power receiving part 111 according to the present embodiment includes the first slider and the second slider, two sets of cords in which every two mechanical cords 230 are paired may be respectively controlled in an effective manner.

In some embodiments, the power receiving part 111 may be a pair of power receiving parts. One of the pair of power receiving parts may control the upward and downward bending of the bendable section 141, and the other of the pair of power receiving parts may control the left and right bending of the bendable section 141. The pair of power receiving parts 111 may include a first slider and a second slider. The first slider may control the upward and downward bending motion of the bendable section 141, and the second slider may control the left and right bending motion of the bendable section 141.

According to this structure, the first slider and the second slider may move linearly and independently of each other.

Due to the combination of the linear movements of the first slider and the second slider, the upward and downward bending and the left and right bending of the bendable section 141 may be combined, thereby realizing the bending motion in upward-downward and left-right directions.

Figure 6:
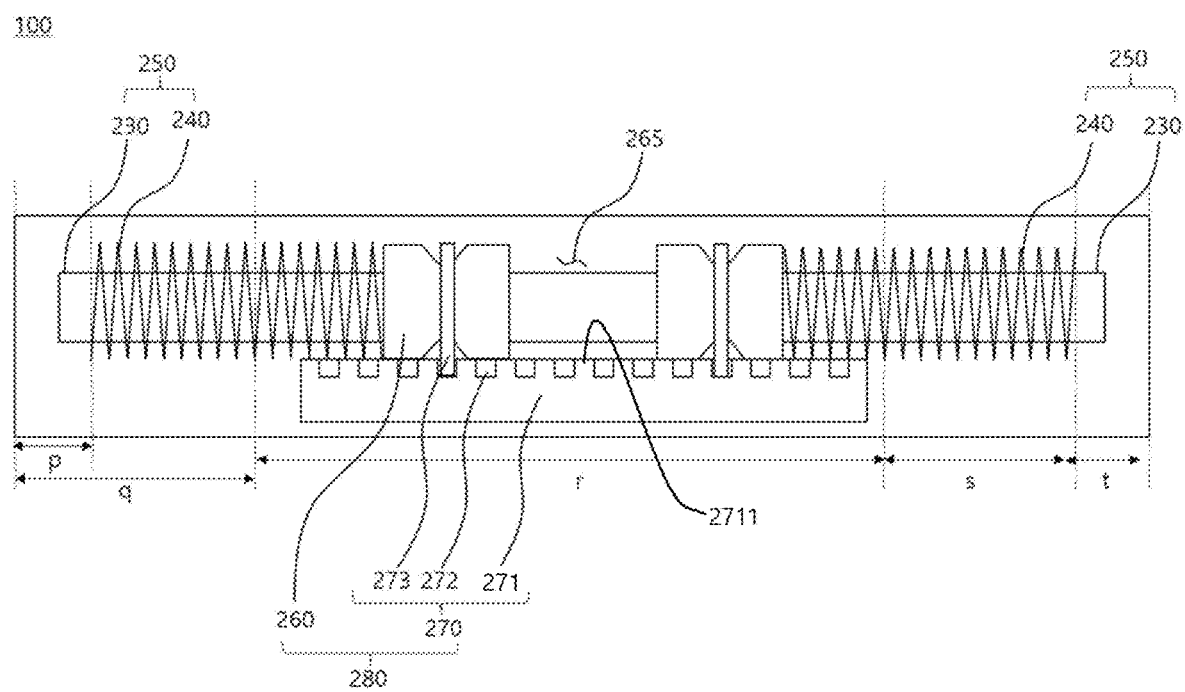
FIG. 6 illustrates a schematic shape of a friction control part provided on a power transmission means according to an embodiment of the present disclosure.

FIG. 6 illustrates a schematic shape of a friction control part provided on a power transmission means according to an embodiment of the present disclosure.

Figure 7:
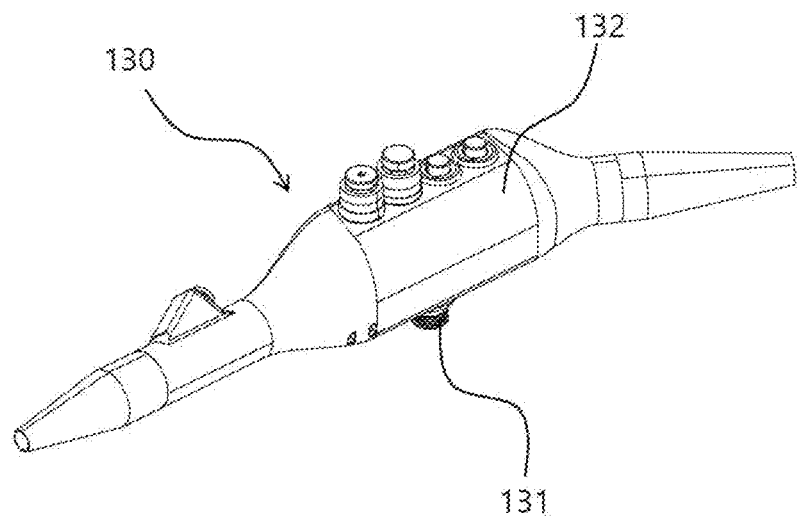
FIG. 7 illustrates the shape of the control body according to an embodiment of the present disclosure.
Figure 8:
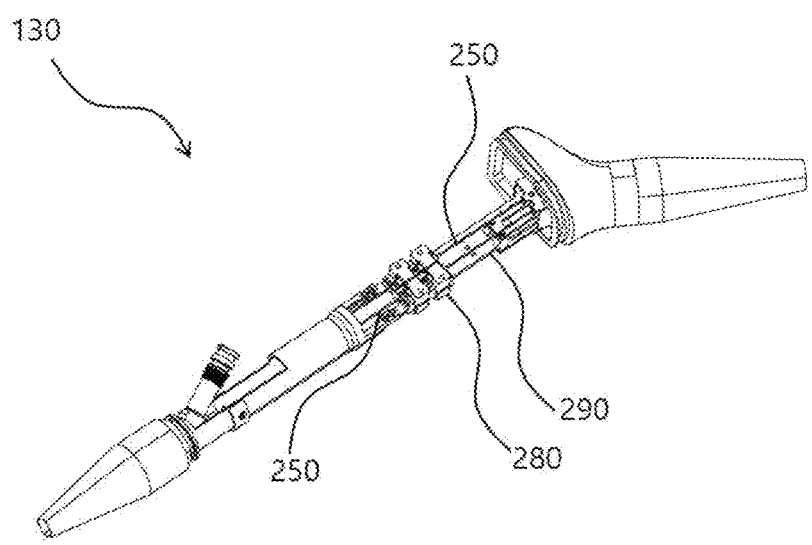
FIG. 8 illustrates the control body of FIG. 7 from which the cover case is omitted.

FIG. 7 illustrates the shape of the control body according to an embodiment of the present disclosure, and FIG. 8 illustrates the control body of FIG. 7 from which the cover case is omitted.

Figure 9:
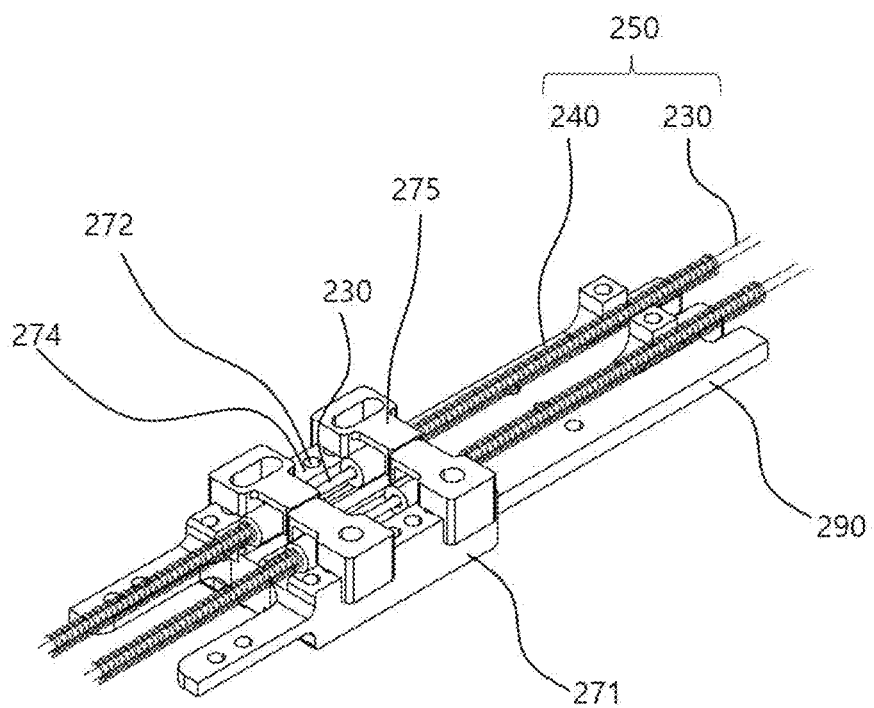
FIG. 9 illustrates the shape of the power transmission means and the friction control part in the control body of FIG. 8.
Figure 10:
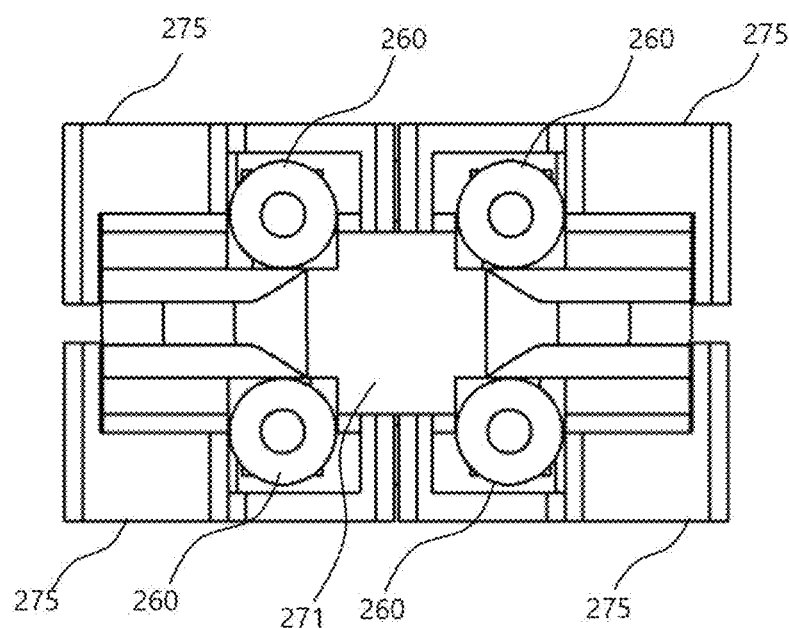
FIG. 10 illustrates the cross-sectional shape of the friction control part illustrated in FIG. 9.

FIG. 9 illustrates the shape of the power transmission means and the friction control part in the control body of FIG. 8, and FIG. 10 illustrates the cross-sectional shape of the friction control part illustrated in FIG. 9.

Figure 11:
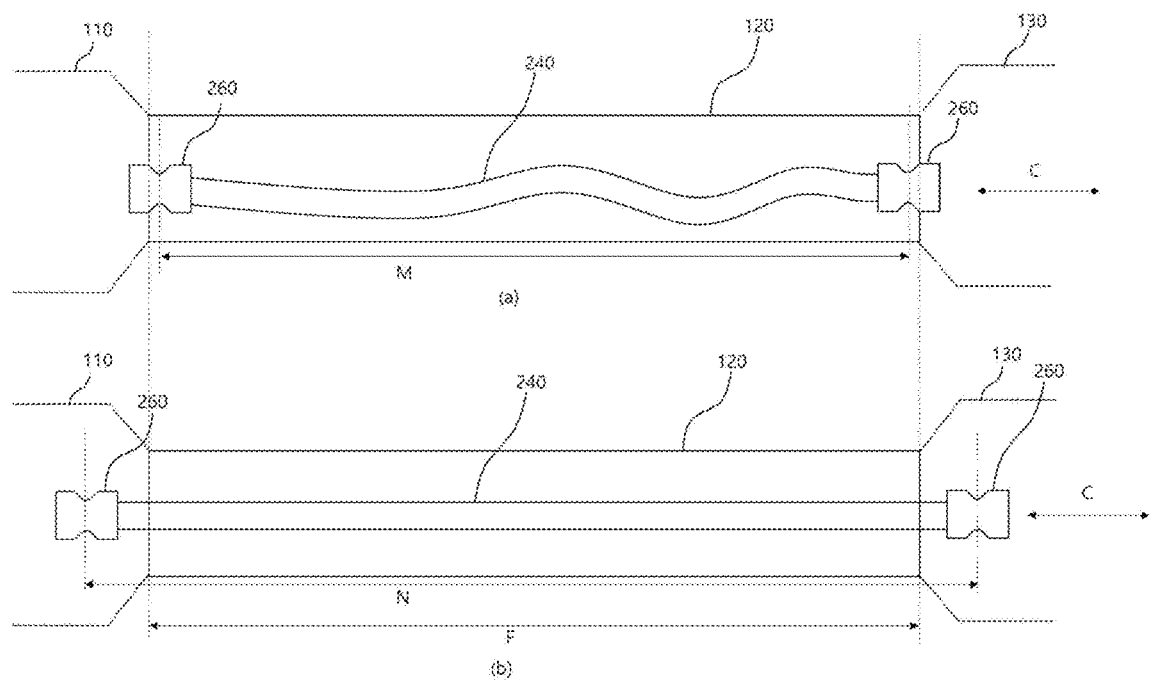
FIG. 11 illustrates the shape of the guide tube disposed within the universal cord in the power transmission means according to an embodiment of the present disclosure.

FIG. 11 illustrates the shape of the guide tube disposed within the universal cord in the power transmission means according to an embodiment of the present disclosure.

Figure 12:
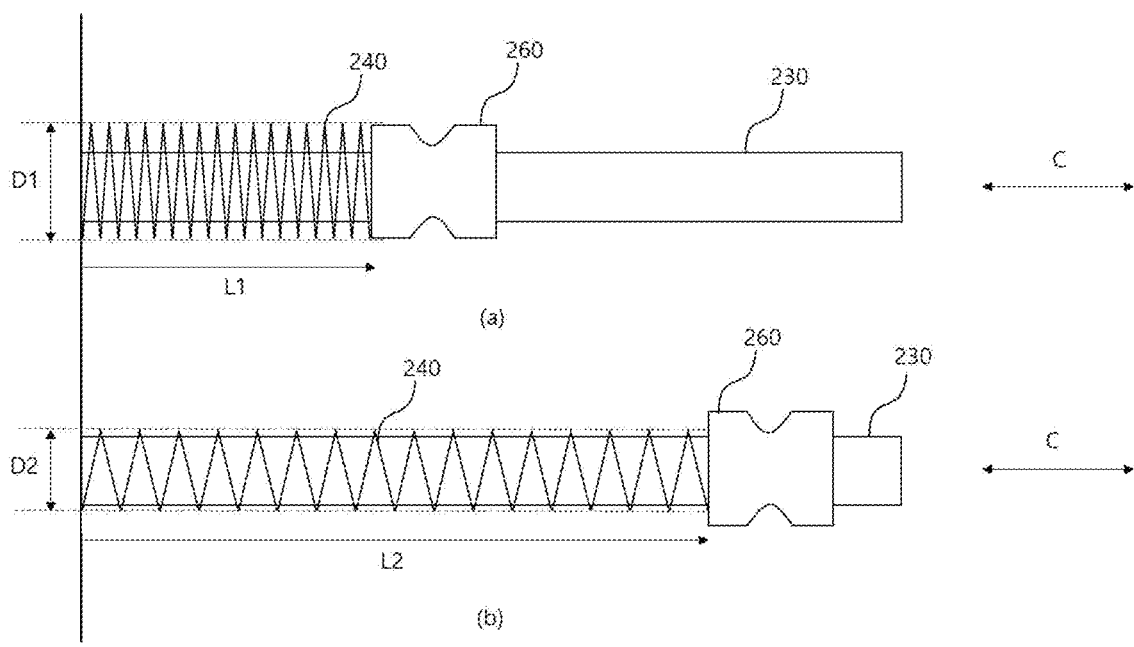
FIG. 12 illustrates the shape of the spring structure and the end holding part according to an embodiment of the guide tube surrounding the mechanical cord in the power transmission means according to an embodiment of the present disclosure.

FIG. 12 illustrates the shape of the spring structure and the end holding part according to an embodiment of the guide tube surrounding the mechanical cord in the power transmission means according to an embodiment of the present disclosure.

According to an embodiment of the present disclosure, there may be provided an endoscope 100 including: the bendable section 141 configured to be inserted into the subject's body to collect image information; and a power transmission means 250 for transmitting power received from the power source to the bendable section 141, wherein the power transmission means 250 includes the power-transmitting mechanical cords 230 and a friction control part 280 restraining the movement of the mechanical cords 230.

In the present embodiment, the power transmission means 250 may perform the function of transmitting power received in the connector 110 to the bendable section 141. The power transmission means 250 may include the mechanical cords 230 and guide tubes 240 surrounding and protecting the mechanical cords 230. In this structure, the mechanical cords 230 may transmit power while axially moving within the guide tubes 240.

The power transmission means 250 according to the present embodiment may extend in the longitudinal direction of the endoscope 100, and may have a structure connecting the connector 110 provided on one end of the endoscope 100 and the bendable section 141 provided on the other end of the endoscope 100. Due to this structure, the power transmission means 250 may transmit power stored in the connector 110 to the bendable section 141, thereby allowing the bendable section 141 to perform the bending motion.

In some embodiments, the power transmission means 250 may include a plurality of power transmission means. The power transmission means 250 may be, for example, four power transmission means. That is, the four mechanical cords 230 including the first cord 231, the second cord 232, the third cord, and the fourth cord and the guide tubes 240 may be included. As described above, in this structure, the first cord 231 and the second cord 232 may be paired to move together, and the third cord and the fourth cord may also be paired to move together.

In the present embodiment, the friction control part 280 may be provided on a portion of the power transmission means 250, and may perform the function of restraining the axial movement of the mechanical cords 230 in the power transmission means 250. When the power transmission means 250 includes a plurality of power transmission means, the friction control part 280 may be disposed on each of the plurality of power transmission means. When the power transmission means 250 are four, two friction control parts may be disposed on the top surface of a fixed block 271 described below and the other two friction control parts may be disposed on the bottom surface of the fixed block 271.

As the power transmission means 250 is longer, increases in the length of the mechanical cords 230 may delay power transmission or cause backlash, thereby making it difficult to uniformly transmit power. In particular, in a structure in which the connector 110 is supplied with power from an external source and the power that the connector 110 has received is transmitted to the bendable section 141 through the universal cord 120, the control body 130, and the insertion tube 140, the power transmission means 250 extends from the connector 110 to the bendable section 141 to increase the lengths of the mechanical cords 230, thereby deteriorating the above-described responsiveness. In order to overcome these problems, the present disclosure may restrain the axial movement of the mechanical cords 230 so that power transmission through the mechanical cords 230 may be uniformly output. That is, in the present disclosure, the friction control part 280 may provide resistance to the axial movement of the mechanical cords 230, thereby preventing rattling during movement.

In the power transmission means 250 according to an embodiment of the present disclosure, the friction control part 280 may be disposed in any section of the longitudinal section of the power transmission means 250. In some embodiments, the friction control part 280 may be provided in the control body 130 or the connector 110.

Referring to FIG. 6, section p indicates the section of the bendable section 141, section q indicates the section of the insertion tube 140, section r indicates the section of the control body 130, section s indicates the section of the universal cord 120, and section t indicates the section of the connector 110. When the power transmission means 250 is formed to extend over the entire section of the endoscope 100 from the connector 110 to the bendable section 141, the responsiveness of the bending motion may be reduced. Thus, the role of the friction control part 280 is important.

The control body 130 or the connector 110 is a component in which parts performing a variety of functions are disposed. In the control body 130 or the connector 110, a space capable of accommodating the friction control part 280 may be formed. Thus, it may be more effective that the friction control part 280 according to the present embodiment is provided in the control body 130 or the connector 110 rather than in the insertion tube 140 or the universal tube.

In some embodiments, the control body 130 may include a body cover 132 and a body frame 290 disposed within the body cover 132. A portion of the body frame 290 may form a fixing means 270 described below. The fixing means 270 is a component of the friction control part 280. The power transmission means 250 may be disposed and extend on the body frame 290.

In addition, since the friction control part 280 may include the fixing means 270 described below, the friction control part 280 may reduce the flexibility of the insertion tube 140 or the universal cord 120 when disposed on the insertion tube 140 or the universal cord 120. Thus, it may be effective that the friction control part 280 is disposed on the control body 130 or the connector 110.

In some embodiments, the friction control part 280 of the endoscope 100 according to the present embodiment may include a restraint control part provided to control the movement restraint of the mechanical cords 230.

In addition to the friction control part 280 restraining the axial movement of the mechanical cords 230 using the restraint control part according to the present disclosure, the degree of restraint for restraining the axial movement of the mechanical cords 230 may be variously adjusted.

When fabricating the endoscope 100 according to the present embodiment, a fabricator may set optimal responsiveness by performing a responsiveness test on the bending motion of the bendable section 141 by the restraint control part according to the present embodiment.

In some embodiments, in the power transmission means 250 including the mechanical cords 230 and the guide tubes 240, the friction control part 280 may restrain the movement of the mechanical cords 230 by adjusting the diameters of the guide tubes 240. The guide tubes 240 have a structure extending along with the mechanical cords 230 in the longitudinal direction of the mechanical cords 230 and entirely surrounding the mechanical cords 230. Thus, the movement of the mechanical cords 230 within the guide tubes 240 may be restrained by adjusting the diameters of the guide tubes 240. The method of adjusting the diameters of the guide tubes 240 may provide uniform and continuous pressing over the entire length of the mechanical cords 230 and thus is effective in improving responsiveness.

In some embodiments, the guide tubes 240 may include a spring structure. In addition, the friction control part 280 according to the present embodiment may adjust the diameter of the spring structure by pulling or pushing the spring structure of the guide tubes 240.

The spring structure is structured such that the diameter thereof decreases when pulled in the longitudinal direction.

Thus, the spring structure is effective for realizing the friction control part 280 according to the present embodiment. According to the present embodiment, the fabricator of the endoscope 100 may adjust the diameters of the guide tubes 240 by pulling or pushing the guide tubes 240 having the spring structure.

For example, when the diameter of the guide tube 240 is greater than the diameter of the mechanical cord 230 and thus the interior of the guide tube 240 is loose, the restraint of the movement of the mechanical cord 230 decreases. When the diameter of the guide tube 240 is similar to the diameter of the mechanical cord 230, the interior of the guide tube 240 is tightly fitted to the mechanical cord 230, and the restraint of the movement of the mechanical cord 230 increases. In this manner, the movement of the mechanical cords 230 may be restrained.

Herein, the control of friction occurring during the movement of the mechanical cords 230 may include both a method of controlling friction occurring during the movement of the mechanical cords 230 by adjusting the tension of the guide tubes 240 and a method of controlling friction occurring during the movement of the mechanical cords 230 by adjusting the diameters of the guide tubes 240.

In FIG. 11, both FIGS. 11 (a) and (b) illustrate the guide tubes 240 located within the universal cord 120. FIG. 11 (a) illustrates the shape of a wavy guide tube 240 located within the universal cord 120, and FIG. 11 (b) illustrates the shape of the guide tube 240 tautly disposed by pulling end holding parts disposed on both ends of the guide tube 240 in the axial direction C from the position of FIG. 11 (a).

Referring to FIG. 11, in FIG. 11 (a), the length M between a pair of end holding parts 260 is shorter than the length E of the universal cord 120. In contrast, in FIG. 11 (b), the length M between the pair of end holding parts 260 is longer than the length F of the universal cord 120. That is, the end holding parts are drawn out from both ends of the universal cord 120 so that the left end holding part is taken out to a portion of the connector 110 and the right end holding part is taken out to a portion of the control body 130. In some embodiments, the end holding parts may be fixedly disposed at the positions of the connector 110 and the control body 130, respectively.

When fabricating the endoscope according to the present embodiment, the fabricator locates the power transmission means within the universal cord 120. Here, the diameter of the universal cord 120 is significantly greater than the diameter of the power transmission means. Thus, the power transmission means is placed in a wavy shape within the universal cord 120 (see FIG. 11 (a)). When the power transmission means is disposed in such a wavy shape, the mechanical cord 230 within the guide tube 240 is subjected to strong friction when moving in the longitudinal direction C within the guide tube 240. Thus, the mechanical cord 230 may not move smoothly.

Such friction makes it difficult to accurately transmit power to the bendable section and, as a result, reduces accuracy in the position control of the bendable section.

In the friction control part according to the present embodiment, the end holding parts disposed on both ends of the guide tube 240 are respectively pulled and fixed, so the power transmission means is pulled and disposed flat within the universal cord 120. Thus, friction occurring when the mechanical cord 230 moves within the guide tube 240 may be minimized, thereby allowing the mechanical cord 230 to move smoothly.

In FIG. 11 (b), the end holding part is pulled so that the outer circumferential surface of the guide tube 240 is relatively in parallel to the inner circumferential surface of the universal cord 120. Moreover, FIG. 12 (b) illustrates the shape of the end holding part pulled more than in FIG. 11 (b). When the end holding part continues to be pulled, beyond the point where the guide tube 240 is parallel to the universal cord 120, the diameter of the guide tube 240 begins to change. As the end holding part is pulled further, the length of the guide tubs 240 increases, while the diameter of the guide tube 240 decreases. These features will be described later.

Referring to FIG. 12, FIG. 12 (a) illustrates the shape of the end holding part 260 pulled by L1, and FIG. 12 (b) illustrates the shape of the end holding part 260 pulled by L1. When the end holding part 260 is pulled by L1, the diameter of the guide tube 240 is D1. In contrast, when the end holding part 260 is pulled by L2 longer than L1, the diameter of the guide tube 240 is reduced to D2. Thus, the space between the guide tube 240 and the mechanical cord 230 is reduced, so it is difficult for the mechanical cord 230 to move in the axial direction C.

In some embodiments, the friction control part 280 may include the end holding parts 260 connected to respective ends of the guide tubes 240 from which the mechanical cords 230 are drawn and the fixing means 270 on which the end holding parts 260 are disposed.

The friction control part 280 according to the present embodiment may include a structure in which the mechanical cords 230 extend through the guide tubes 240 and are drawn out from the distal ends of the guide tubes 240, respectively. In this structure, the end holding parts 260 may be provided on the distal ends of the guide tubes 240, and the end holding parts 260 may be fixedly disposed on the fixing means 270.

The end holding parts 260 may have any configuration within the scope of technical concept including a structure by which the end holding parts 260 may be fixed to the fixing means 270 in a state in which the guide tubes 240 are pulled and tensioned. In some embodiments, the end holding parts 260 may have the shape of a dumbbell, i.e., a cylinder having a reduced-thickness central portion.

The fixing means 270 according to the present embodiment may perform the function of fixing the end holding parts 260. In some embodiments, the fixing means 270 may be disposed on the body frame 290 disposed within the control body 130.

In some embodiments, the fixing means 270 may include a position control part capable of adjusting positions at which the end holding parts 260 are disposed in order to control the movement restraint of the mechanical cords 230.

The position control part may be a component having substantially the same function as the above-described restraint control part.

In some embodiments, the fixing means 270 may include the fixed block 271 and fixing brackets 275. Here, the fixed block 271 may be provided on the body frame 290 disposed within the above-described control body 130. In some embodiments, the fixed block 271 may be a portion of the body frame 290.

The fixing brackets 275 may have the function of fixing the end holding parts 260 of the guide tubes 240 to the fixed block 271. In some embodiments, the fixed block 271 may be provided with a guide wall 274 configured to guide and support the end holding parts 260 on both sides, and a plurality of fastening holes 272 may be sequentially formed at predetermined distances in the top surface of the guide wall 274. The end holding parts 260 may be fixed by fixedly disposing each of the fixing brackets 275 to a corresponding one among the plurality of fastening holes 272 using a fastening means 273 such as a bolt or a nut.

Here, in some embodiments, the position control part may have a plurality of fastening holes 272 formed in the guide wall 274 of the fixed block 271. The fabricator may adjust the diameter of the guide tubes 240 by fitting each of the end holding parts 260 to a corresponding one among the plurality of fastening holes 272, followed by fixing with the fixing brackets 275, and then stretching the guide tubes 240 by predetermined values.

According to another aspect of the present disclosure, in some embodiments, the power transmission means 250 may include the mechanical cords 230 and the guide tubes 240 configured to surround and guide the mechanical cords 230. In the power transmission means 250, portions of guide tubes 240 may be torn to form a structure 265 by which the mechanical cords 230 are exposed externally.

In this manner, the endoscope 100 may include the fixing means 270 able to fix the separated both ends of each of the guide tubes 240 by pulling or pushing the same in the structure 265 in which the portions of the guide tubes 240 are torn and separated such that the mechanical cords 230 are exposed externally.

The above-described end holding parts 260 may be disposed on the separated ends of the guide tubes 240, and the end holding parts 260 may adjust the diameters of the guide tubes 240 by pulling the guide tubes 240, thereby restraining the movement of the mechanical cords 230.

The components according to the present embodiment may be the same as the components according to the foregoing embodiments. Thus, a detailed description of the components according to the present embodiment will be omitted.

Another aspect of the present disclosure may provide an endoscope 100 including one or more among: an insertion tube 140 including a bendable section 141 configured to be inserted into a subject's body to perform a bending motion;
a control body 130 connected to the insertion tube 140 and configured to be held by a user; a connector 110 connected to the control body 130 and configured to receive power from an external source; a universal cord 120 spacing the control body 130 and the connector 110 apart from each other; a power transmission means 250 configured to receive power from the connector 110 and transmit the same to the bendable section 141; and
a friction providing part provided on one side of the power transmission means 250 and configured to provide friction to the power transmission means 250.

Herein, in some embodiments, the friction providing part providing friction to the power transmission means 250 may indicate that in the case in which the power transmission means 250 includes a power cable through which power is transmitted and guide tubes 240 having a structure surrounding the power cable, when the power cable moves within the guide tubes 240, friction is provided. In the present embodiment, the friction providing part may perform substantially the same function as the friction control part 280 according to the foregoing embodiment. In addition, in the present embodiment, other components may be substantially the same function as the components according to the foregoing embodiment. Accordingly, a detailed description of the other components will be omitted.

In the specification of the present disclosure, the use of the term "the or said" and similar denoting terms may correspond to both singular and plural forms. Furthermore, recitation of ranges of values herein are merely intended to values falling within the refer to respective separate respective ranges and, unless otherwise indicated herein, the respective separate values are incorporated herein as if individually recited herein.

The operations of any method described herein may be performed in any suitable order unless otherwise indicated herein or otherwise clearly contradicted by the context. However, the operations shall not be limited to the described sequence. The use of any examples or exemplary languages (e.g., "such as") provided herein, is intended merely to better illustrate the present disclosure and does not pose a limitation on the scope of the present disclosure unless otherwise defined by the Claims. In addition, a person having ordinary knowledge in the art will appreciate that various modifications, combinations, and changes are possible according to design conditions and factors within the scope of the Claims or equivalents thereof.

Therefore, the spirit of the present disclosure shall not be limited to the above-described embodiments, and the entire scope of the appended claims and equivalents thereof will fall within the scope and spirit of the present disclosure.

<Description of Reference Numerals of Drawings>

| | |
|---|---|
| 100: endoscope | 110: connector |
| 111: power receiving part | 111a: protrusion |
| 112: front cover | 113: slot |
| 120: universal cord | 130: control body |
| 131: controller | 132: body cover |
| 140: insertion tube | 141: bendable section |
| 200: rail structure | |
| 210: pinion-sprocket assembly | |
| 211: pinion gear | 212: sprocket |
| 220: chain-slider assembly | 221: chain |
| 222: slider | 230: mechanical cord |
| 231: first cord | 232: second cord |
| 240: guide tube | |

<Description of Reference Numerals of Drawings>

| | |
|---|---|
| 250: power transmission means | |
| 260: end holding part | |
| 270: fixing means | |
| 271: fixed block | 272: fastening hole |
| 273: fastening means | 274: guide wall |
| 275: fixing bracket | 280: friction control part |
| 290: body frame | 300: light source device |
| 310: power providing part | 311: recess |
| 320: connector receptacle | d: travel distance |

The invention claimed is:

1. An endoscope comprising:
a bendable section configured to be inserted into a subject's body to collect image information; and
a power transmission means configured to transmit power provided by a power source to the bendable section to allow the bendable section to perform a bending motion,
wherein the power transmission means comprises:
a power-transmitting mechanical cord and a friction control part configured to promote or restrain a movement of the mechanical cord;
a control body connected to the bendable section and configured to control a bending motion of the bendable section; and
a connector connected to the control body,
wherein one side of the power transmission means is connected to the connector, and the other side of the power transmission means extends through the control body and is connected to the bendable section,
the connector receives the power from the power source and transmits the power to the power transmission means,
the power transmission means comprises a guide tube surrounding the mechanical cord to guide the same, and the friction control part controls friction occurring during the movement of the mechanical cord by adjusting a diameter of the guide tube or a tension of the guide tube,
the friction control part comprises an end holding part connected to one end of the guide tube from which the mechanical cord is drawn and a fixing means on which the end holding part is disposed, the end holding part including first, second, third, and fourth end holding parts, and
the fixing means comprises a fixed block and a fixing bracket fixing the end holding part to the fixed block, the fixed block comprising a partition provided on one side thereof and supporting the end holding part and a plurality of fastening holes sequentially provided in the partition, and the fixing bracket being fixedly fitted to one of the plurality of fastening holes using a fastening means,
wherein the partition is formed of multiple partitions and the multiple partitions are formed respectively at an upper left, an upper right, a lower left, and a lower right of the fixed block, each of the multiple partitions supporting each of the first, second, third, and fourth end holding parts.

2. The endoscope of claim 1, wherein the friction control part is provided on the control body or the connector.

3. The endoscope of claim 1, wherein the guide tube comprises a spring structure, and the friction control part adjusts the diameter of the spring structure or the tension of the guide tube by pulling or pushing the spring structure.

* * * * *